United States Patent [19]

Pulido et al.

[11] Patent Number: 4,983,618
[45] Date of Patent: Jan. 8, 1991

[54] COMBINATION OF 2-(THIOCYANOMETHYLTHIO)BENZO-THIAZOLE AND A TRIHALOGENATED PHENOL

[75] Inventors: Miguel L. Pulido, Memphis, Tenn.; Juan M. Ayzaguer, Santiago, Chile

[73] Assignee: Buckman Laboratories International, Inc., Memphis, Tenn.

[21] Appl. No.: 380,117

[22] Filed: Jul. 14, 1989

[51] Int. Cl.$^5$ .................. A01N 31/08; A01N 43/78
[52] U.S. Cl. .................................. 514/367; 514/737; 252/106
[58] Field of Search ............... 514/367, 737; 252/106

[56] References Cited

U.S. PATENT DOCUMENTS

| | | | |
|---|---|---|---|
| 3,520,976 | 7/1970 | Buckman et al. | 514/367 |
| 4,290,846 | 9/1981 | Muntwyler | 514/737 |
| 4,388,215 | 6/1983 | Ishida et al. | 514/367 |
| 4,479,961 | 10/1984 | Martin | 424/270 |

FOREIGN PATENT DOCUMENTS

| | | |
|---|---|---|
| 266110 | 5/1988 | European Pat. Off. |
| 55-059907 | 5/1980 | Japan. |
| 56-075412 | 6/1981 | Japan. |
| 58-118505 | 7/1983 | Japan. |
| 61-41501 | 2/1986 | Japan .................. 514/367 |
| 63-101305 | 5/1988 | Japan. |

OTHER PUBLICATIONS

Derwent Publications English language abstract of Jpn. Pat. Doc. 63-101305.
Derwent Publications English language abstract of Jpn. Pat. Doc. 58-118505.
Derwent Publications English language abstract of Jpn. Pat. Doc. 56-075412.
Derwent Publications English language abstract of Jpn. Pat. Doc. 55-059907.
Derwent Publications English language abstract of Jpn. Pat. Doc. 61-041501.

Primary Examiner—Allen J. Robinson
Attorney, Agent, or Firm—Finnegan, Henderson, Farabow, Garrett and Dunner

[57] ABSTRACT

2-(thiocyanomethylthio) benzothiazole and at least one tri-halogenated phenol, preferably 2,4,6-tribromophenol, are used, preferably in synergistic amounts, to control microbiological growth.

23 Claims, No Drawings

COMBINATION OF 2-(THIOCYANOMETHYLTHIO)BENZOTHIAZOLE AND A TRIHALOGENATED PHENOL

BACKGROUND OF THE INVENTION

This invention relates to compositions of 2-(thiocyanoethylthio)benzothiazole (TCMTB) and at least one trihalogenated phenol for the purpose of controlling the growth and reproduction of microorganisms.

More particularly, the invention relates to compositions containing TCMTB and at least one trihalogenated phenol to inhibit the growth of fungi and bacteria in industrial processes and products. For example, fungi are traditionally classified as a subdivision of the Thallophyta of the plant kingdom and are saprophytic or parasitic, i.e., fungi must derive their nutrition from a preformed source of organic carbon. Spore dispersal mechanisms among the fungi provide an effective means of extending the species to sources of organic and mineral nutrition, provided that existing temperature and moisture conditions are conducive for growth of the organism.

The spores germinate into vegetative hyphae which are capable of degrading the organic substrate on which they are growing, yielding smaller and simpler subunits These in turn are absorbed into the body of the fungus whereby they are metabolized, and the organism derives nutrients or builds cellular structures.

Such degradative processes are important in nature because they constitute a means of recycling organic debris which collects on the surface of the earth However, other vehicles of nutrition are provided by industry since fungi do not discriminate between what is perceived by man to be harmful versus what is perceived to be beneficial.

One such source of energy is raw, unseasoned wood produced from the activities of sawmills The cut logs represent a rich source of organic and inorganic compounds contained within a moist cellulosic matrix. At sawmills, raw or freshly cut lumber is characteristically stacked outdoors for air drying (cure).

During this relatively slow process of drying, the lumber is continuously being contaminated with fungal spores whose germination and growth on the wood surface may lead to significant economic loss to the sawmill as a result of surface disfigurement due to sapstain and/or mold. In addition, other fungal species may contaminate the wood and then actually decay or diminish the structural integrity of the wood by enzymatically hydrolyzing the cellulose and/or lignin within the primary and secondary cell walls.

In the lumber industry, these fungal problems are controlled through the application of chemicals to the freshly cut wood. Among commercially available chemicals which have experienced use in this industry are pentachlorophenol (PCP), 2-(thiocyanomethylthio) benzothiazole (TCMTB) (available commercially from Buckman Laboratories, Inc.), 3-iodopropynylbutylcarbamate (IPBC), and disodium octaborate tetrahydrate (available commercially as Tim-Bor ®)

Some of the organic fungicidal agents, such as PCP, are the objects of increasing environmental concern resulting in legal restrictions on, or complete banning of, their usage. The discovery of synergistic combinations of chemicals which include TCMTB provides an opportunity to achieve a desired level of protection of wood against fungal spoilage at a reduced quantity of chemical consumption and at a potentially lower cost.

The chemical TCMTB is a known fungicide which is used commercially for the protection of freshly cut lumber against mold and sapstain. Combinations of TCMTB with other fungistatic materials to provide synergistic compositions have been reported for bis-trichloro-methyl-sulfone (U.S. Pat. No. 4,479,961), 3-iodopropynyl--N-butyl carbamate (Japan Pat. No. 63,101,305), and methylene-bisthiocyanate (Japanese Patent No. 61,041,501). Additional patents have described the use of 2,4,6-tribromophenol alone or in combination with other substances for wood protection (Japan Pat. Nos. 58,118,505, 56,075,412 and 55,059,907).

None of these patents, however, describes the combination of TCMTB and at least one trihalogenated phenol, such as 2,4,6-tribromophenol. The composition of this invention contains TCMTB and at least one trihalogenated phenol and, preferably, a synergistic combination of TCMTB and at least one trihalogenated phenol. These compositions can be effective for controlling microbiological growth and particularly fungal growth.

The compositions of the invention can protect surfaces in general against microorganisms such as fungi. Representative surfaces which can be protected include wood, leather, textiles paint, plastics, paper and pulp which are subject to attack by microorganisms such as fungi. The compositions can also inhibit the growth of microorganisms, such as bacteria and fungi in liquid and solid substrates, such as dyes, pastes and adhesives, and, particularly in liquid and solid substrates associated with industrial processes.

SUMMARY OF THE INVENTION

The composition of the present invention can effectively control all forms of microbiological growth and, specifically, can control the growth of the microorganisms causing lumber sapstain such as the fungi *Aureobasidium pullulans, Ceratocystis sp.,* and others, as well as molds such as *Trichoderma sc.* The composition that has been found effective for controlling microorganisms comprises a combination of 2-(thiocyanomethylthio) benzothiazole and at least one trihalogenated phenol, preferably, 2,4,6-tribromophenol (tribromophenol) (TBP). In a preferred embodiment of the invention, at least one trihalogenated phenol, such as TBP, and TCMTB are combined in synergistic amounts. Preferably, when synergistic amounts of trihalogenated phenol and TCMTB are utilized, the weight ratio of trihalogenated phenol to TCMTB ranges from about 25/75 to 75/25.

DETAILED DESCRIPTION OF THE PREFERRED EMBODIMENTS

As mentioned above, TCMTB is a commercially available chemical. In may be obtained, for example, from Buckman Laboratories, Inc., Memphis, Tenn.

Trihalogenated phenols are also commercially available chemicals As mentioned, TBp, the preferred trihalogenated phenol, is described in the patent literature Amounts of TCMTB and trihalogenated phenol to be used will vary according to the particular microorganism sought to be controlled in a particular environment. Effective amounts in general, and synergistically effective amounts in particular, of TCMTB and trihalogenated phenol can be routinely determined by one skilled in the art for any particular application.

For example, for controlling fungal growth, an amount of TCMTB and trihalogenated phenol providing at least 4000 ppm (0.4%) of total active ingredient can be used. For controlling bactericidal growth, an amount of TCMTB and trihalogenated phenol providing at least 500 ppm can be used.

The composition of the invention may be prepared in liquid form by dissolving the TCMTB and at least one trihalogenated phenol in an organic solvent Suitable organic solvents are well-known and can be routinely selected by one skilled in the art. The liquid form of the invention is particularly useful to prevent the decay and molding of starch paste, wet pulp, and wood.

The composition of the invention may also be prepared in emulsion form by emulsifying the TCMTB and trihalogenated phenol in water and, if necessary, adding a surfactant. Suitable surfactants are well-known and can be routinely selected by one skilled in the art.

A demonstration of the synergistic interaction between TCMTB and TBP is presented in the following two examples These examples are illustrative only and in no way limit the invention.

EXAMPLE 1

The biological activities of the individual components and their mixture was determined according to the procedure described by A.J. Cserjesi and J.W. Roff in "Accelerated Laboratory Test for Evaluating Toxicity of Fungicides for Lumber " Mater. Res. Stand. 10(3):18–19, 59–60 (1970), as follows The synergism of the two components, TCMTB and TBP, (with data and calculations provided below) was demonstrated by adding the TCMTB with tribromophenol. The purified, technical grade ingredients were mixed in varying ratios over a range of concentrations in acetone. The solutions used for treatment also included a concentration series of each component by itself These solutions were used to treat freshly cut pine sapwood coupons $3 \times 5 \times 0.3$ cm). The autoclaved coupons were individually immersed in the treatment solutions with gentle agitation for ten seconds, and then placed horizontally on a screen to air-dry for 24 hours.

Incubation units for the treated wood were prepared by inserting into sterile petri plates ($10 \times 1.5$ cm) a layer comprising four discs of moist, sterile Whatman 1 filter paper (7cm diameter). Onto the paper was placed a sterile V-shaped glass rod which provided support for the wood coupon above the moist paper.

The treated and dried coupon was placed on the glass rod, and the upper surface of the wood was inoculated with four drops of a spore suspension of the mold Trichoderma. The covered petri dishes were incubated at 28° C. for two weeks at which time the wood treatments were evaluated based on the degree of fungal infestation.

The lowest concentration of each compound or mixture required for complete prevention of sapstain or mold was taken as the end point. End points for the mixtures of the compounds were then compared with the end points for the individual compounds alone.

Synergism was determined by the method described by F.C. Kull et al., "Mixtures of Quaternary Ammonium Compounds and LongChain Fatty Acids as Antifungal Agents," *Applied Microbiology* 9:538–541 (1961), employing the ratio determined by:

$$Qa/QA = Qb/QB$$

wherein, $QA$ = solution percent of Compound A acting alone which produced an end point.

$QB$ = solution percent of Compound B acting alone which produced an end point.

$Qa$ = solution percent of Compound A in the mixture which produced an end point.

$Qb$ = solution percent of Compound B in the mixture which produced an end point.

When the sum of $Qa/QA$ and $Qb/QB$ is greater than one, antagonism is indicated, and when the sum is equal to one, additivity is indicated. When the sum is less than one, synergism is demonstrated.

The Kull et al. procedure for demonstrating the synergism of the compositions of this invention is a widely used and accepted procedure. More detailed information is provided in the article by Kull et al.

Table I shows the percent control data of the mold Trichoderma from the laboratory experiment according to the procedure described above. As mentioned above, these data result from a concentration series of each compound alone, as well as from mixtures of the two ingredients.

TABLE I

| Tribromo-phenol (% w/w) | TCMTB (% w/w) | | | |
|---|---|---|---|---|
| | 0.0 % control | 0.2 % control | 0.6 % control | 0.8 % control |
| 0.0 | 0 | 26 | 40 | 100 |
| 0.4 | 0 | 93 | 100 | 100 |
| 0.6 | 46 | — | 93 | 80 |
| 0.8 | 76 | 80 | 96 | 93 |

The data demonstrate that a treatment with TCMTB alone required a concentration of 0.8% active ingredient on a weight basis to provide total control of the mold Trichoderma. The highest concentration of tribromophenol tested (0.8%) alone did not provide complete or essentially complete prevention of mold infestation (75%).

A treatment solution, however, which contained a mixture of the two compounds (0.2% TCMTB + 0.4% tribromophenol) provided essentially complete prevention of the mold attack (93%). Therefore, the following values may be applied tOward the method of Kull et al., with subsequent calculation of the sum of the ratios:

| From the TCMTB data: | $QA = 0.8$ | $Qa = 0.2$ |
|---|---|---|
| From the tribromophenol data: | $QB > 0.8$ | $Qb = 0.4$ |
| Consequently, $Qa/QA + Qb/QB$ | $= 0.2/0.8 + 0.4/(>0.8)$ | |
| | $= 0.25 + (<0.5) < 1.0$ | |

Since the sum of the indicated ratios is less than one, an action of synergism is shown for a mixture of TCMTB and tribromophenol in preventing mold on the wood.

EXAMPLE 2

The data provided in Table II relative to the control of sapstain induced by fungi such as *Ceratocystis sp.* and molds such as *Trichoderma sp.* were summarized from data generated by two consecutive field tests utilizing formulations of the subject ingredients. Woodstakes ($5 \times 10 \times 40$ cm. or longer) were dipped in aqueous suspensions of the formulated active ingredients in a series of concentrations.

Sixteen stakes per each of three replications of each chemical treatment were prepared After an appropriate incubation time outdoors, the stakes were evaluated for degree of infestation by sapstain induced by fungi such as Ceratocystis and molds such as Trichoderma.

The commercial product TCMTB 30, emulsifiable concentrate (30% of active TCMTB), was the source of TCMTB; tribromophenol was provided as a solution containing 400 g active ingredient per liter, and the combination of the two ingredients was an emulsifiable concentrate containing a total of 20% active ingredient on a weight basis (split equally between TCMTB and tribromophenol on a weight basis).

TABLE II

| Treatment | Dosage (% ai)* | Ceratocystis % control | Trichoderma % control |
|---|---|---|---|
| Control | 0 | 0 | — |
| TCMTB 30 | 0.6 | 100 | 85 |
| | 1.2 | 100 | 92 |
| | 1.8 | 100 | 100 |
| Tribromophenol | 0.8 | 85 | 100 |
| | 1.2 | 90 | 100 |
| | 1.6 | 97 | 100 |
| | 2.0 | 99 | 100 |
| | 4.0 | 99.5 | 100 |
| | 4.8 | 100 | 100 |
| | 6.0 | 100 | 100 |
| Tribromophenol + | 0.45 | 95 | 99.4 |
| TCMTB | 0.67 | 98.8 | 100 |
| (1:1 wt ratio) | 0.90 | 99.2 | 100 |

*"ai" stands for active ingredient.

Commercially, tribromophenol is recommended at 8% v/v in water of the 400 g per liter concentrate for securing the control of sapstain. This dosage is equivalent to 32,000 ppm of active ingredient tribromophenol in the treatment solution.

In this trial, a concentration of 16,000 ppm of tribromophenol (1.6% ai) was required to achieve 97 percent control or prevention of Ceratocystis fungal-caused stain on the wood. Furthermore, 18,000 ppm of TCMTB (1.8% ai) was required for obtaining 100 percent control or prevention of the mold Trichoderma.

In contrast, the formulated combination of the TBP and TCMTB ingredients provided essentially complete prevention of stain at a concentration which contained only 0.67% total active ingredient (equivalent to 3350 ppm of TCMTB plus 3360 ppm of tribromophenol).

The sapstain fungi such as Ceratocystis sp. and the molds such as Trichoderma sp. are competitive fungal microorganisms. Thus, the presence of one on a piece of lumber is antagonistic to the growth of the other.

A purpose of a preferred embodiment of the invention is to have a combination of fungicides that will simultaneously control both sapstain and mold fungi.

As seen from Table II, the combination of the two active components TBP and TCMTB can provide a synergism in controlling mold and sapstain on wood. The concentration of total active ingredient in the mixture which provides complete control is greatly reduced below the concentration of either component alone required to achieve the same level of effectiveness.

We claim:

1. A composition for controlling microbiological growth comprising a synergistically effective microbiocidal amount of the combination of 2-(thiocyanomethylthio) benzothiazole and tribromophenol.

2. The composition of claim 1, wherein the weight ratio of the phenol to the benzothiazole ranges from about 25/75 to 75/25.

3. The composition of claim 1, wherein said phenol is 2,4,6-tribromophenol.

4. A method for controlling microbiological growth comprising the step of incorporating in or applying to a surface in need of microbiological growth control an effective amount of the composition of claim 1.

5. The method of claim 4, wherein said phenol is 2,4,6-tribromophenol.

6. The method of claim 4, wherein said surface is selected from the group consisting of wood, leather, textiles, paint, plastics, paper and pulp.

7. The method of claim 4, wherein the weight ratio of the phenol to the benzothiazole ranges from about 25/75 to 75/25.

8. The method of claim 4, wherein said microbiological growth in need of control is Trichoderma sp.

9. The method of claim 8, wherein said surface is wood.

10. The method of claim 4, wherein said microbiological growth is Ceratocystis sp.

11. The method of claim 10, wherein said surface is wood.

12. A method of inhibiting the growth of a microorganism comprising the step of contacting said microorganism with an effective amount of the composition of claim 1.

13. The method of claim 12, wherein said microorganism is selected from the group consisting of Aureobasidium pullulans Ceratocystis sp., and Trichoderma sp.

14. The method of claim 12, wherein said phenol is 2,4,6-tribromophenol.

15. The method of claim 12, wherein the weight ratio of the phenol to the benzothiazole ranges from about 25/75 to 75/25.

16. The method of claim 12, wherein said microorganism is inhibited in a liquid substrate.

17. The method of claim 13, wherein said microorganism is inhibited in a solid substrate.

18. The method of claim 12, wherein said microorganism is inhibited in a liquid substrate selected from the group consisting of dyes, pastes and adhesives.

19. A method of preventing decay or deterioration of a material capable of supporting growth of a microorganism comprising the step of contacting said material with an effective amount of the composition of claim 1.

20. The method of claim 19, wherein said microorganism is selected from the group consisting of Aureobasidium pullalans, Ceratocystis sp., and Trichoderma sp.

21. The method of claim 19, wherein said phenol is 2,4,6-tribromophenol.

22. The method of claim 19, wherein the weight ratio of the phenol to the benzothiazole ranges from about 25/75 to 75/25.

23. The method of claim 19, wherein said material is wood.

* * * * *